United States Patent [19]
Whitehead et al.

[11] Patent Number: 5,921,991
[45] Date of Patent: Jul. 13, 1999

[54] MULTI-COLORED UMBILICAL CORD CLAMP

[75] Inventors: Peter D. Whitehead; Christopher R. Thompson, both of West Vancouver, Canada

[73] Assignee: Biomax Technologies Inc., Vancouver, Canada

[21] Appl. No.: 08/956,976

[22] Filed: Oct. 23, 1997

[51] Int. Cl.[6] ................................................. A61B 17/42
[52] U.S. Cl. ........................... 606/120; 606/119; 606/157; 606/158
[58] Field of Search .................................. 606/120, 157, 606/158, 151, 119

[56] References Cited

U.S. PATENT DOCUMENTS

| | | | |
|---|---|---|---|
| 3,247,852 | 4/1966 | Schneider | 128/346 |
| 3,825,012 | 7/1974 | Nicoll | 606/120 |
| 4,026,294 | 5/1977 | Mattler | 128/305 |
| 4,212,303 | 7/1980 | Nolan | 606/120 |
| 4,428,374 | 1/1984 | Auburn | 128/318 |
| 4,716,886 | 1/1988 | Schulman et al. | 128/305 |
| 5,127,915 | 7/1992 | Mattson | 606/120 |
| 5,423,831 | 6/1995 | Nates | 606/120 |
| 5,608,382 | 3/1997 | Webb et al. | 606/120 |

*Primary Examiner*—Michael Buiz
*Assistant Examiner*—Lien Ngo
*Attorney, Agent, or Firm*—Seed and Berry LLP

[57] ABSTRACT

The present invention provides umbilical cord clamps that comprise two or more different colors at the distal end of each of the elongated arms of the clamps. The colors are complementary to each other so that, when combined, they create a third color.

11 Claims, 1 Drawing Sheet

MULTI-COLORED UMBILICAL CORD CLAMP

TECHNICAL FIELD

The technical field of the present invention relates to umbilical cord clamps.

BACKGROUND OF THE INVENTION

The umbilical cord of an infant is a tubular structure that connects the fetus with the placenta. The cord exchanges waste products, oxygen and nutrients between the mother and the fetus. Upon the baby's birth, the umbilical cord has traditionally been severed by the placement of two clamps at two points along the cord, and then cutting the cord between the clamped points. A variety of umbilical cord clamps are well known in the art. Exemplary clamps are disclosed in U.S. Pat. No. 3,247,852 to Schneider, U.S. Pat. No. 4,716,886 to Schulman, U.S. Pat. No. 5,423,831 to Nates, and U.S. Pat. No. 5,608,382 to Webb. (These references, and all other references cited herein, are hereby incorporated by reference in their entirety.)

A critical feature of an umbilical cord clamp is that the clamp must not come off the cord after the cord has been severed. Accordingly, it is necessary for the user to determine that the clamp has been completely closed, thereby minimizing the risk that the clamp will fall off the cord or slip off the end of the severed cord. Thus, there has gone unmet a need for an umbilical cord clamp that comprises a visual display that indicates to the user that the clamp has been completely closed. The present invention provides this and other related advantages.

SUMMARY OF THE INVENTION

The present invention provides devices and methods comprising umbilical cord clamps that comprise at least two different colors at the distal end of each of the arms of the clamps, wherein the different colors are complementary to each other such that, when combined (e.g., when one color is laid over or juxtaposed relative to the other), the colors create a third color. For example, if a tooth that projects from one arm is a yellow color, and a corresponding opening in the other arm comprises one or more translucent or transparent walls that are blue, then inserting the tooth into the opening causes the blue color and the yellow color to combine to make a third color, green. The third color is not created until the tooth has been securely, completely engaged in the opening, thereby providing the user with a visible assurance that the clamp has been completely closed. Such assurance of complete closure decreases the likelihood that the clamp will slip off the end of the umbilical cord once it has been severed and/or will simply fall off because the clamp was not completely closed.

Thus, in one aspect the present invention provides an improvement in umbilical cord clamps of the type having first and second arms connected to each other, each arm having an engagement section for engaging the surface of the umbilical cord and each arm movable relative to one another to cause the engagement sections to clamp the umbilical cord when the arms are moved together, wherein the improvement comprises a projection having at least a portion thereof of a first color connected to the first arm and projecting toward the second arm, wherein the second arm includes a portion thereof forming an opening juxtaposed to the colored portion of the projection when the umbilical cord has been clamped, a translucent or transparent window mounted in the opening, the window comprising a second color that is different from the first color, so that upon moving the arms together to close the clamp, the first and second colors combine to create at least one third color that is different from the first and second colors and that is visible to a user of the clamp to indicate that the clamp is closed.

In a preferred embodiment, the portion of the second arm which forms the opening forms a well which receives the projection on the first arm. In other preferred embodiments, the clamp further includes a first latch member element connected to the first arm and a second latch member element connected to the second arm which link together to retain the arms together when the umbilical cord is adequately compressed and wherein the third color is not created until the latch members are so linked, and the colors are non-body colors, further preferably fluorescent colors such as fluorescent yellow, blue and red, giving rise to the creation of fluorescent green, orange or purple.

In one preferred embodiment, the projection connected to the first arm comprises a tooth having an enlarged head at least the top of which is of the first color, wherein a plurality of circumferentially disposed, inwardly projecting, resilient spring flaps are disposed in the opening in the second arm to receive and captively retain the head of the tooth when the umbilical cord is adequately compressed, wherein the opening in the second arm has a first end which receives the tooth and a second end opposite the first and wherein the window covers the second end of the opening in the second member.

In another aspect, the present invention provides umbilical cord clamps comprising first and second arms each having a proximal end and a distal end, the arms being flexibly connected at the proximal ends for movement together to clamp an umbilical cord of an infant, the distal end of the first arm having a first latch element, the distal end of the second arm having a second latch element which link to retain the arms together when the umbilical cord is adequately compressed, wherein the arms further comprise means for creating a color when the latches are engaged to secure the arms together.

In still another aspect, the present invention provides methods of clamping an umbilical cord of an infant comprising the following steps: placing any of the umbilical cord clamps described herein around the umbilical cord; inserting the tooth or projection of the first arm into or adjacent the opening of the second arm; viewing the distal ends of the first and second arms to determine whether at least one color has been created, and considering the tooth to be securably engaged within the opening, or the clamp closed, where the color has been created and to not be securably engaged within the opening, or closed, where the color has not been created.

In one preferred embodiment, the method further comprises, upon determining the color has not been created, inserting the tooth or projection more deeply into the opening, thereby securably engaging the tooth in the opening, or closing the clamp, and creating the color.

These and other aspects of the present invention will become evident upon reference to the following detailed description and the attached drawings. In addition, various references are set forth herein that describe in more detail certain procedures or compositions (e.g., different styles of umbilical cord clamps); all such references are incorporated herein by reference in their entirety.

DETAILED DESCRIPTION OF THE INVENTION

The present invention provides umbilical cord clamps that comprise two or more different colors at the distal end of each of the elongated arms of the clamps. The colors are complementary to each other so that, when combined, such as by juxtaposing one relative to the other or laying one over the other, they create a third color. For example, if a tooth that projects from one arm is a red color, and the corresponding opening in the other arm comprises one or more translucent or transparent walls, or windows, that are blue, then inserting the tooth into the opening causes the blue color and the red color to combine to make purple. The creation of the third color indicates that the tooth has been securely, completely engaged in the opening. In other words the latch, in this case formed in part by the tooth, has engaged to retain the clamp in a position that adequately compresses the umbilical cord. This assurance of complete closure of the clamp increases the safety of the clamp.

A wide variety of styles of umbilical cord clamps are well known in the art. See, e.g., U.S. Pat. No. 3,247,852 to Schneider, U.S. Pat. No. 4,716,886 to Schulman, U.S. Pat. No. 5,423,831 to Nates, and U.S. Pat. No. 5,608,382 to Webb. It will be a routine matter for a person of ordinary skill in the art, in light of the present invention, to modify these or other known umbilical cord clamps to incorporate the use of at least two different, complementary colors in the catch mechanisms of the umbilical cord clamps to thereby to provide a third color upon completed closure of the clamp. Thus, the figures set forth herein represent merely one embodiment of the claimed invention.

Figure 1:
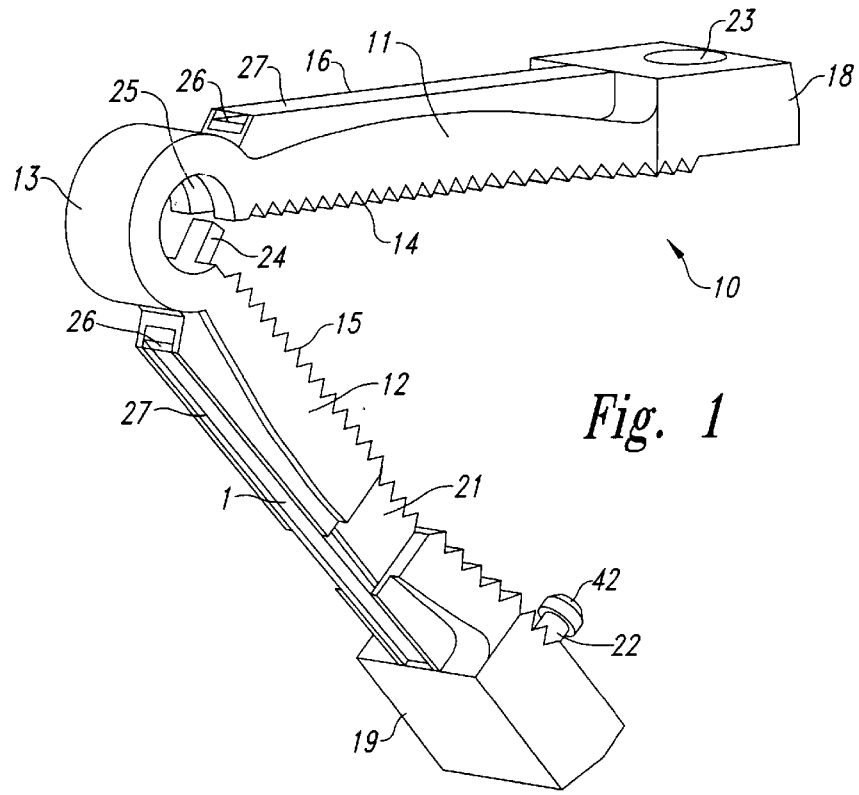
FIG. 1 is a side perspective view of an umbilical cord clamp according to the present invention.

Turning to FIG. 1, the present invention provides an umbilical cord clamp 10 made of a flexible material, preferably a plastic such as nylon, although other materials are also suitable for use within the present invention. Clamp 10 includes a pair of elongated arms 11 and 12, each of which has a distal end and a proximal end. The proximal ends of arms 11 and 12 are flexibly connected to each other via a flexible hinge 13, typically to form a pair of jaws in a "V" shape. Arms 11 and 12 can be closed by pressing the distal ends of the arms (which can comprise grip portions 18 and 19) toward each other. Arms 11 and 12 includes serrated surfaces 14 and 15 on their inner sides. Such surfaces provide a strong grip on the umbilical cord when the clamp is closed about the cord. If desired, arms 11 and 12 can also comprise channels 16 and 17, which comprise transparent plastic sheets 27 and identification information elements 26 disposed therein, to aid in identification of the infant, which is typically a human baby. Preferably, a resilient bar 24 is attached to the proximal end of arm 12, and a slot 25 is arranged on the inner side of hinge 13 near the proximal end of arm 11. Such a bar 24 prevents the umbilical cord (not shown) from slipping into the opening of the hinge 13.

Arm 12 comprises a tooth 22 comprising a colored head 42. Tooth 22 is a projection that is disposed on the inner side of grip portion 19 and extends toward arm 11. An opening 34, which is a hole or other receiving area, is positioned within the inner side of grip portion 18 on arm 11 so as to receive tooth 22. Opening 34 is covered on the outer side of grip portion 18 by transparent or translucent window 23, which window thereby forms a wall of opening 34; such transparency or translucency can also be located in a side wall of opening 34. Colored head 42 comprises a first color and colored window 23 comprises a second, complementary color, such that when colored head 42 is disposed adjacent to, and preferably in contact with, colored window 23, the two colors combine to create a third color. By complementary, it is meant two or more colors that form a distinct third color when they are combined. For example, if the first and second colors are blue and yellow, then the third color will be green; if the first and second colors and red and yellow, the third color will be orange; if the first and second colors are blue and red, the third color will be violet or purple. Preferably, the colors are selected to be non-body colors, which means colors that are not traditionally found within the human body, such as the colors of blood, the external surface of an umbilical cord, etc. In one preferred embodiment, such non-body colors are fluorescent colors, further preferably yellow, blue and green.

Figure 2:
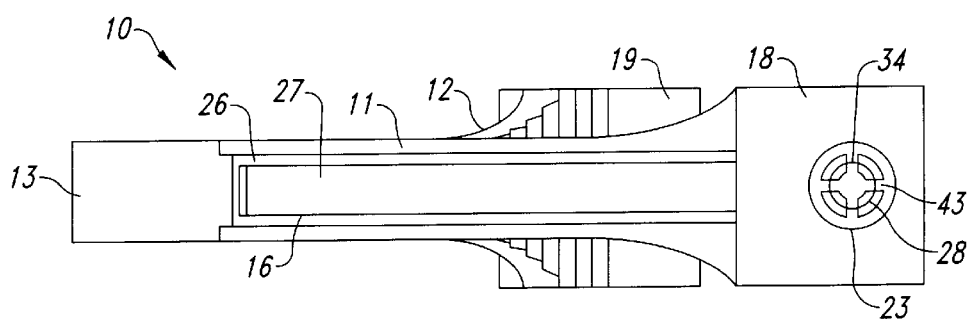
FIG. 2 is a top view of an umbilical cord clamp.

FIG. 2 depicts a top view of clamp 10 and shows colored window 23 disposed atop opening 34. Within the opening are found circumstantially disposed, inwardly projecting, resilient spring flaps 28 and shoulder 43, which cooperate to securably, which means tightly and non-releasably, engage tooth 22 (and therefore enlarged colored head 42) when such tooth is completely inserted into opening 34.

Figure 3:
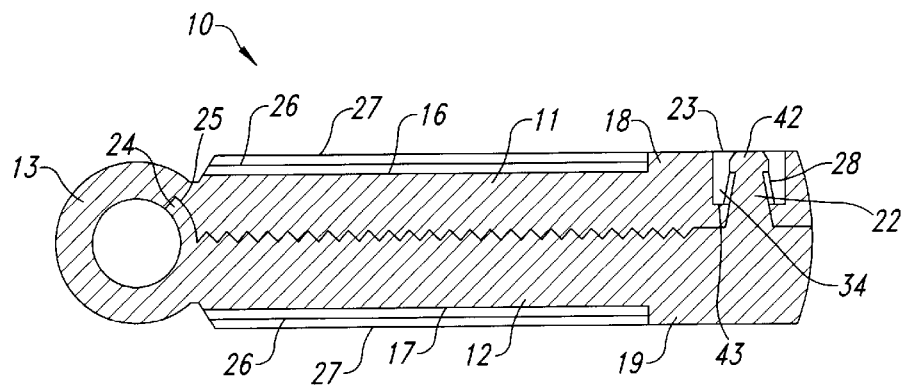
FIG. 3 is a side cross-sectional view of the umbilical cord clamp.

Turning to FIG. 3, the umbilical cord clamp 10 is depicted in closed position (in practice it would be closed about an umbilical cord, but such is not shown in the present illustration for purposes of clarity). Briefly, arms 11 and 12 are pressed together so that tooth 22 is pushed through opening 34 until enlarged head 42 is snapped past spring flaps 28. The distal ends of inwardly-angled spring flaps 28 engage the lower rim of head 42 to lock arms 11 and 12 together. Spring flaps 28 are preferably recessed deep within hole 23 to prevent tampering. Once locked in place, tooth 22 cannot be pulled back out of hole 34. In addition, when clamp 10 is closed, resilient bar 24 is forced into conformity within curved slot 25, thereby preventing passage of the umbilical cord into the hinge 13. Preferably, and as depicted in FIG. 3, enlarged head 42 is physically contacted with colored window 23. This promotes creation of the third color, particularly when window 23 is translucent instead of transparent (translucent indicates that the window transmits light but is not clear; transparent indicates that the window is clear, other than its color).

If the clamp must be removed, then a conventional clamp cutting tool (not shown) can be used to cut the clamp at constricted neck portion 21, or elsewhere along the clamp if deemed desirable.

From the foregoing it will be appreciated that, although specific embodiments of the invention have been described herein for purposes of illustration, various modifications may be made without deviating from the spirit and scope of the invention. Accordingly, the invention is not limited except as by the appended claims.

We claim:

1. An improvement in an umbilical cord clamp of the type having first and second arms connected to each other, each arm having an engagement section for engaging the surface of the umbilical cord and each arm movable relative to one another to cause the engagement sections to clamp the umbilical cord when the arms are moved together, wherein the improvement comprises a projection having at least a portion thereof of a first color connected to the first arm and projecting toward the second arm, wherein the second arm includes a portion thereof forming an opening juxtaposed to the colored portion of the projection when the umbilical cord has been clamped, a translucent or transparent window mounted in the opening, the window comprising a second color that is different from the first color, so that upon moving the arms together to close the clamp, the first and second colors combine to create at least one third color that is different from the first and second colors and that is visible to a user of the clamp to indicate that the clamp is closed.

2. The improved umbilical cord clamp of claim 1, wherein the portion of the second arm which forms the opening forms a well which receives the projection on the first arm.

3. The improved umbilical cord clamp of claim 1 wherein the clamp further includes a first latch member element connected to the first arm and a second latch member element connected to the second arm which link together to retain the arms together when the umbilical cord is adequately compressed and wherein the third color is not created until the latch members are so linked.

4. The improved umbilical cord clamp of claim 1 wherein the colors are non-body colors.

5. The improved umbilical cord clamp of claim 1 wherein the first color is fluorescent yellow, the second color is fluorescent blue and the third color is fluorescent green.

6. The improved umbilical cord clamp of claim 1 wherein the projection connected to the first arm comprises a tooth having an enlarged head at least the top of which is of the first color, wherein a plurality of circumferentially disposed, inwardly projecting, resilient spring flaps are disposed in the opening in the second arm to receive and captively retain the head of the tooth when the umbilical cord is adequately compressed, wherein the opening in the second arm has a first end which receives the tooth and a second end opposite the first and wherein the window covers the second end of the opening in the second member.

7. An umbilical cord clamp comprising first and second arms each having a proximal end and a distal end, the arms being flexibly connected at the proximal ends for movement together to clamp an umbilical cord of an infant, the distal end of the first arm having a first latch element, the distal end of the second arm having a second latch element which link to retain the arms together when the umbilical cord is adequately compressed, wherein the arms further comprise means for creating a color when the latches are engaged to secure the arms together.

8. A method of clamping an umbilical cord of an infant comprising the following steps:

placing an umbilical cord clamp according to any one of claims 1 to 7 around the umbilical cord;

moving the projection of the first arm adjacent the opening of the second arm;

comparing the distal ends of the first and second arms to indicate whether the movement of the projection adjacent to the opening has created at least one color, wherein the clamp is closed where at least one color has been created and is not closed where at least one color has not been created.

9. The method of claim 8 wherein the projection comprises a tooth and the opening forms a well which receives the projection, and wherein the method further comprises, upon determining the color has not been created, inserting the tooth more deeply into the opening, thereby securably engaging the tooth in the opening and creating the color.

10. The method of claim 8 wherein the color is a non-body color.

11. The method of claim 10 wherein the color is fluorescent green.

* * * * *